(12) United States Patent
Bartholomeusz

(10) Patent No.: US 12,303,470 B2
(45) Date of Patent: May 20, 2025

(54) METHOD AND COMPOSITION FOR SELECTIVE TREATMENT OF ANDROGEN RECEPTORS

(71) Applicant: SKINQRI, LLC, Lincolnshire, IL (US)

(72) Inventor: James Bartholomeusz, Beverly Hills, CA (US)

(73) Assignee: SKINQRI, LLC, Lincolnshire, IL (US)

( * ) Notice: Subject to any disclaimer, the term of this patent is extended or adjusted under 35 U.S.C. 154(b) by 0 days.

(21) Appl. No.: 17/337,548

(22) Filed: Jun. 3, 2021

(65) Prior Publication Data

US 2022/0387353 A1 Dec. 8, 2022

(51) Int. Cl.
*A61K 31/12* (2006.01)
*A61K 41/00* (2020.01)
*A61K 45/06* (2006.01)

(52) U.S. Cl.
CPC .......... *A61K 31/12* (2013.01); *A61K 41/0057* (2013.01); *A61K 45/06* (2013.01)

(58) Field of Classification Search
CPC .... A61K 41/0057; A61K 45/06; A61K 31/12; A61K 9/0021
See application file for complete search history.

(56) References Cited

U.S. PATENT DOCUMENTS

| | | |
|---|---|---|
| 7,095,569 B2 | 8/2006 | Rege et al. |
| 7,241,731 B2 | 7/2007 | Hirai et al. |
| 7,404,498 B2 | 7/2008 | Hattori et al. |
| 7,560,428 B2 | 7/2009 | Hirai et al. |
| 7,750,115 B2 | 7/2010 | Oka et al. |
| 8,198,323 B2 | 6/2012 | Lee |
| 8,846,611 B2 | 9/2014 | Oh |
| 9,173,921 B1 | 11/2015 | Lim |
| 9,446,127 B2 | 9/2016 | Shih |
| 10,894,074 B2 | 1/2021 | Bartholomeusz |
| 2008/0317733 A1 | 12/2008 | Azimi |
| 2011/0081802 A1 | 4/2011 | Knepp |
| 2012/0021029 A1 | 1/2012 | Sanz et al. |
| 2012/0039837 A1 | 2/2012 | Somfleth et al. |
| 2012/0054034 A1 | 3/2012 | Mattingly et al. |
| 2012/0065131 A1 | 3/2012 | Dake et al. |
| 2012/0123305 A1 | 5/2012 | Pearl |
| 2013/0011356 A1 | 1/2013 | Fahnestock et al. |
| 2014/0069452 A1 | 3/2014 | Krueger |
| 2015/0265516 A1 | 9/2015 | Anzali et al. |
| 2015/0272860 A1 | 10/2015 | Mette et al. |
| 2016/0116295 A1 | 4/2016 | Singh |
| 2016/0199282 A1 | 7/2016 | Wiesche et al. |
| 2016/0199498 A1 | 7/2016 | Dai et al. |
| 2019/0134142 A1* | 5/2019 | Bartholomeusz .... A61K 9/0014 |
| 2020/0315949 A1 | 10/2020 | Morley |

FOREIGN PATENT DOCUMENTS

| | | |
|---|---|---|
| EP | 0455422 A2 | 11/1991 |
| KR | 100802144 B1 | 2/2008 |
| WO | WO2003039596 * 5/2003 | ............ A61K 41/00 |
| WO | 2017010597 A1 | 1/2017 |
| WO | 2017146514 A1 | 8/2017 |

OTHER PUBLICATIONS

Vegamour "Gro+ Advanced Hair Serum" (https://vegamour.com/products/gro-advanced-hair-serum/; accessed Nov. 17, 2022; archived via WayBack Machine Aug. 12, 2020) (Year: 2020).*
Singh et al., The role of surfactants in the formulation of elastic liposomal gels containing a synthetic opioid analgesic, 2016, International Journal of Nanomedicine, 11, 1475-1482 (Year: 2016).*
Kazantzis et al., Curcumin derivatives as photosensitizers in photodynamic therapy: photophysical properties and in vitro studies with prostate cancer cells, 2020, Photochem. Photobiol. Sci., 19, 193-206 (Year: 2020).*
Niu et al., Red Light Combined with Blue Light Irradiation Regulates Proliferation and Apoptosis in Skin Keratinocytes in Combination with Low Concentrations of Curcumin, 2015, PLOS ONE, 10, 1-18 (Year: 2015).*
Webmd, Anti-Androgens for Hair Loss: Everything You Need to Know, https://www.webmd.com/connect-to-care/hair-loss/what-to-know-about-anti-androgens-for-hair-loss; accessed Dec. 2, 2022; archived via Wayback Machine Feb. 19, 2021 (Year: 2021).*
Paolillo et al., The effect of combined curcumin-mediated photodynamic therapy and artificial skin on *Staphylococcus aureus*-infected wounds in rats, 2020, Lasers in Medical Science, 36, 1219-1226 (Year: 2020).*
Chen et al., Preparation of Curcumin-Loaded Liposomes and Evaluation of Their Skin Permeation and Pharmacodynamics, 2012, Molecules, 17, 5972-5987 (Year: 2012).*
Alghadir et al., Efficacy of Curcumin with Iontophoretic Application on Paw Edema and Hematological Responses in Collagen-Induced Arthritis Rat Models, 2020, Evid Based Complement Alternat Med., 2020, 1-11 (Year: 2020).*
Kocaadam et al., Curcumin, an active component of turmeric (*Curcuma longa*), and its effects on health, 2017, Crit Rev Food Sci Nutr., 13, 2889-2895 (Year: 2017).*
Hamblin, Mechanisms and applications of the anti-inflammatory effects of photobiomodulation, AIMS Biophys, 2017, 4(3), 337-361 (Year: 2017).*
Vanić et al., Phospholipid Vesicles for Enhanced Drug Delivery in Dermatology, Journal of Drug Discovery, Development and Delivery, 2015, 2(1), 1-9, ISSN: 2471-0288 (Year: 2015).*

(Continued)

*Primary Examiner* — Mark V Stevens
(74) *Attorney, Agent, or Firm* — McDonald Hopkins LLC

(57) ABSTRACT

An improved method of promoting hair growth includes the use of one or more photosensitive curcuminoids, provided in combination with other hair growth components and preferably solubilized in bio-compatible materials to create a nano-particulate. These materials are introduced via fractional topical delivery and subsequently activated by exposure to specific wavelengths of light. This sequence results in improved hair growth in comparison to previously known methods, and the use of photosensitive curcuminoids in this manner may be employed to treat other skin disorders.

19 Claims, 1 Drawing Sheet

(56) References Cited

OTHER PUBLICATIONS

Waghule et al., Emerging Trends in Topical Delivery of Curcumin Through Lipid Nanocarriers: Effectiveness in Skin Disorders, 2020, AAPS PharmSciTech, 21, DOI: 10.1208/s12249-020-01831-9 (Year: 2020).*
Lintzeri et al., Epidermal thickness in healthy humans: a systematic review and meta-analysis, 2022, JEADV,36,1191-1200, DOI: 10.1111/jdv.18123 (Year: 2022).*
Crowther et al., Measuring the effects of topical moisturizers on changes in stratum corneum thickness, water gradients and hydration in vivo, 2008, British Journal of Dermatology, 159, 567-577, DOI: 10.1111/j.1365-2133.2008.08703.x (Year: 2008).*
Rachmawati et al (AAPS PharmSciTech, 2013, vol. 14, pp. 1303-1312) (Year: 2013).*
Goncalves et al (Brazilian Journal of Pharmaceutical Sciences, 2014, vol. 50, pp. 885-893) (Year: 2014).*
Vollono et al (Nutrients, Sep. 2019, vol. 11, pp. 1-25) (Year: 2019).*
Niu, T et al. "Red Light Combined with Blue Light Irradiation Regulates Proliferation and Apoptosis in Skin Keratinocytes in Combination with Low Concentrations of Curcumin" 10(9): e0138754. PloS ONE. Online. Sep. 18, 2015.
Singh, A et al. "Curcumin quantum dots mediated degradation of biofilms" 8:1517. Frontiers in Microbiology. Online. Aug. 9, 2017.
Lee, E et al. "Effect of edge activators on the formation and transfection efficiency of ultradeformable Jiposomes" vol. 26, Issue 2. Biomaterials. Online. Mar. 10, 2004; Abstract; p. 2, physicochemical properties of UL and DNNUL complexes.
Singh, S et al. "The role of surfactants in the formulation of elastic liposomal gels containing a synthetic opioid analgesic" 1475-1482. International Journal of nanomedicine. Online. Apr. 8, 2016.
International Searching Authority, US, Patent Cooperation Treaty (PCT), International Search Report and Written Opinion for Application PCT/US2022/31717 filed Jun. 1, 2022, mailed Aug. 30, 2022. https://www.sciencedirect.com/science/article/abs/pii/S1876107016305260?via%3Dihub.

* cited by examiner

METHOD AND COMPOSITION FOR SELECTIVE TREATMENT OF ANDROGEN RECEPTORS

TECHNICAL FIELD

The present invention relates generally to a method and formulation for promoting hair growth and, more particularly, to a fractional topical treatment involving naturally fluorescent materials and nanoliposome-encapsulated blend of growth factors introduced to the targeted skin/scalp area with or without any additional skin barrier destabilization.

BACKGROUND

Hair loss prevention has been a topic of considerable interest. Numerous methods and compounds have been suggested to prevent loss of hair and/or to promote the growth of new hair. These approaches include medications such as finasteride (sold under the brand name Propecia) and minoxidil (sold as Rogaine), as well as individual oligopeptides or growth factors which, on an individual basis, are alleged to prevent hair loss and/or promote hair regeneration and growth.

Generally speaking, a hair follicle—schematically illustrated in FIG. 1—has a three phase life cycle. The anagen phase refers to actual growth, with the root dividing and adding structure and length to the hair shaft itself. The catagen phase is a transitional period from growth to rest, with blood supply being gradually cut off from the cells that normally produce new hair. The final phase, the telogen phase, results in dead hair that may be lost/shed from the scalp. Notably, while the anagen phase involves actual hair growth, it can go on for a period of years and generally includes three specific stages: 1) hair follicle induction; 2) hair follicle morphogenesis; 3) hair formation and growth through maintenance of production and differentiation of stem cell progenitor cells.

U.S. Pat. Nos. 7,750,115; 7,560,428; and 7,241,731 disclose a variety of peptides, peptidic conjugates, and growth factor proteins that are individually alleged to promote hair growth and/or treat hair loss conditions such as alopecia. In the same manner, a number of pending patent publications describe peptides and other compositions in this regard, such as United States Patent Publication 2016/0199282; 2015/0272860; 2015/0265516; 2014/0069452; 2013/0011356; 2012/0065131; 2012/0039837; and 2012/0021029.

These approaches tend to focus strengthening existing hair and/or stimulating new hair growth. Thus, while it is widely understood that the androgen dihydrotestosterone (DHT) plays a causative role in both hirsutism and baldness, these disclosed compositions simply attempt to overcome the deleterious effects of DHT by ensuring the rate of new hair growth outstrips the rate of hair loss.

In contrast, U.S. Pat. No. 8,198,323 describes methods of treating cancer with a wide range of curcuminoid compounds capable of acting as androgen receptor antagonists in order to suppress the effects of DHT. These compounds are defined by various chemical formulae that are structural analogues to curcumin (CAS number 458-37-7), and they are administered via intradermal injection or via transdermal application to address afflictions such as baldness, hirsutism, and acne.

U.S. Pat. No. 9,446,127 discloses an acne treatment in which curcumin is provided topically, while a retinoid is injected. This combination induces androgen receptor degradation to block the creation of DHT.

Major disadvantages to the use of topical curcuminoids are their extremely low solubility in water on one hand, and their strong tendency to stain skin tissue with a yellowish turmeric hue on the other, particularly when applied in high concentrations (as might be needed for transdermal application). Separately, considerable ambiguity exists as to establishing the truly effective amount, and no consideration appears to be given for ways to increase the efficiency/efficacy of the applied substances.

Also, all of the foregoing disclosures do not take into account the cyclic phases of hair growth experienced by each follicle. This apparent oversight represents a missed opportunity insofar as a more holistic approach could selectively target and leverage aspects of the hair growth cycle.

In view of the foregoing, an improved and more effective method of promoting hair growth is needed. Specifically, a methodology that leveraged the advantages of existing compositions and included further enhancements to the efficiency and efficacy of the active constituents would be welcome. Further, a method that avoided the drawbacks of these prior approaches would also be helpful.

SUMMARY

A method of promoting hair growth is contemplated. Specifically, one or a combination of photosensitive curcuminoids are solubilized in the inventive formulations in the forms of free solutes, polymeric micelles, lipid/polymer/phospholipid composites, colloidal nanoparticles, or nanoliposomes. The resulting compound possesses sufficient solubility, both to be provided in various formulations and to be selectively applied to areas of skin where hair growth is desired. Application may involve fractional topical delivery method that allows for uptake of the compound via appropriately sized microchannels inherent to (e.g., skin appendages) or formed in the epidermis. Subsequently, exposure to specific wavelengths of light is employed to improve the efficacy of the hair growth treatment/method.

Specific reference is made to the appended claims, drawings, and description below, all of which disclose elements of the invention. While specific embodiments are identified, it will be understood that elements from one described aspect may be combined with those from a separately identified aspect. In the same manner, a person of ordinary skill will have the requisite understanding of common processes, components, and methods, and this description is intended to encompass and disclose such common aspects even if they are not expressly identified herein.

DESCRIPTION OF THE DRAWINGS

Operation of the invention may be better understood by reference to the detailed description taken in connection with the following illustrations. These appended drawings form part of this specification, and any written information in the drawings should be treated as part of this disclosure. In the same manner, the relative positioning and relationship of the components as shown in these drawings, as well as their function, shape, dimensions, and appearance, may all further inform certain aspects of the invention as if fully rewritten herein.

In the drawings.

DETAILED DESCRIPTION

Figure 1:
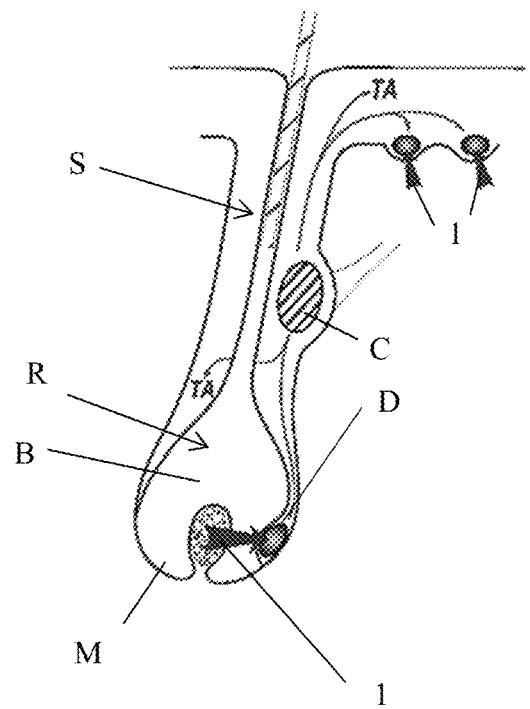
FIG. 1 is a cross sectional side view illustration of a human hair follicle. Hair shaft S extends into the subject's skin connecting to hair root R, which further comprises hair bulb B and hair matrix/papilla M. Bulge-located stem cells C, derivative stem cell populations D, and transient amplifying cells TA are located proximate to these structures, while arrows 1 indicate the modifying influence of adjacent mesenchyme.
Figure 2:
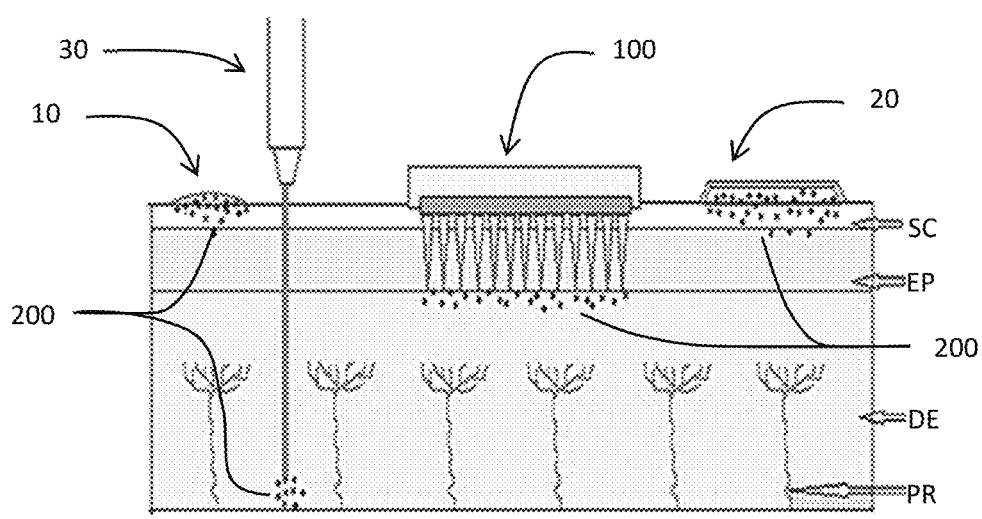
FIG. 2 is a cross sectional side view composite illustration comparing various delivery methods for hair growth compounds 200 on, into, and through the skin. Topical cream 10 and transdermal patch 20 are applied to the stratum corneum SC, which extends 10-40 microns below the skin surface, while hypodermic needle/delivery means 30 deposits compounds 200 at least 1.5 mm or more into the dermis DE proximate to pain receptors PR. Fractional topical delivery methods 100 create microchannels into the epidermis EP at a depth of 50 to 300 microns.

Reference will now be made in detail to exemplary embodiments of the present invention, examples of which are illustrated in the accompanying drawings. It is to be understood that other embodiments may be utilized and structural and functional changes may be made without departing from the respective scope of the invention. As such, the following description is presented by way of illustration only and should not limit in any way the various alternatives and modifications that may be made to the illustrated embodiments and still be within the spirit and scope of the invention.

As used herein, the words "example" and "exemplary" mean an instance, or illustration. The words "example" or "exemplary" do not indicate a key or preferred aspect or embodiment. The word "or" is intended to be inclusive rather an exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

In addition to the phases and stages of hair growth noted above, the inventor realized that each hair follicle independently follow this cycle (i.e., anagen, catagen, and telogen, as well as the specific stages within the anagen phase), so that a substantial portion of hair may at different points in the growth cycle. Thus, by considering these additional stages rather than generically referring to overall hair growth in the anagen phase, the improved methods herein influence hair growth at multiple stages, thereby further improving the likelihood of success.

U.S. Pat. No. 10,894,074 (which is incorporated by reference) discloses a novel combination of growth factors and peptides that has proven useful in promoting hair growth. By providing formulations that address all of the phases, rather than focusing on a single component to influence a single phase or stage, the inventive hair growth methods and formulations achieve improved results in comparison to prior art solutions wherein only a single growth factor or a single stage of the hair growth phase is contemplated. Other examples of growth factors and peptides can be used in combination with or in place of the compositions contemplated by the inventor's previous patent.

Further still, instead of approaching the question of hair loss as one to be treated by orally ingested medication, the inventor deliberately selected an approach that considered topical application. In this manner, the treatment can be more selectively applied, either as a spray or serum. As used herein, it will be understood that topical application means the spray or serum (or whatever form the mixtures of compounds described herein may take) is applied to the surface of the skin without entering the bloodstream or otherwise being ingested by other organs or tissue.

In particular, physical application is by way of fractional topical delivery. This delivery method involves the mechanical or energetic creation of intra-epidermal microchannels. These transient or intrinsic channels form temporary openings to facilitate penetration of the inventive formulations down to hair root itself. In some instances, it may also be possible to achieve the aims of the inventive method by relying on the sheath through which the hair shaft S extends.

With respect to mechanical creation of microchannels, these can be subdivided into dilatation, pressure, and puncture methods. Dilatation may include vasodilating compounds or negative pressure vacuums which effectively open pores and/or create voids in the skin so as to allow the formulation to come into closer proximity with the hair root. In contrast, pressure methods include the application of positive pressure so as to force the formulation into and through the skin, with vibration and massage of exposed skin being examples. Puncture methods contemplate the use of small needles (e.g., 32 gauge needles create ~100 micron openings, although needle gauges between 26 and 34 could be used) or other puncturing apparatus (e.g., sharpened pins having 0.5 to 300 micron openings or resulting in those size range openings after application) that to create a plurality of temporary openings, i.e., microchannels.

Preferably, the needles/pins are provided in a regular, spaced apart ray, possibly extended away from the surface of a roller, flattened pad (either stationary or configured to reciprocate relative to the surface of the skin), or other device that simplifies their use. Also, while consistently sized and spaced punctures are preferred, the mechanical apparatus can be arranged so as to create variability in the overall shape/depth of the microchannels. It is also possible to rely upon a single needle, configured to move in a reciprocating fashion, to allow for creation of localized microchannels with greater precision than might be possible via a roller or pad.

Energetic creation of microchannels may rely on electrical current, sonic energy, and/or electromagnetic radiation. In particular, galvanic current (e.g., iontophoresis) can be applied to the skin open pores. Ultrasonic energy, lasers, visible light (e.g., red light), or radio waves (or other non-visible light) are also possibilities. Notably, some of these additional possibilities create openings in the top layer of the skin by way of fractional injury, while others create a temporary physiological response and/or mimic vibration and direct positive pressure (similar to the mechanical methods noted above) to accomplish the same effects. In each instance, these energetic means may be used in combination with positive pressure to work the formulation into the skin.

Preferably, the openings or voids created by any of the delivery methods above should be about 50 to 500 microns and, more preferably, between 50 and 300 microns in depth (relative to the exterior skin surface). It may be possible to rely on even deeper openings (e.g., less than 1000 microns, less than 750 microns, less than 600 microns, less than 500 microns, etc.), although they should be calibrated to be in proximity with the hair roots and, preferably, not normally extend beyond the epidermis.

The minimum size of the openings (e.g., their diameter or largest width) may not necessarily be dictated by the size of the solubilized curcuminoids or growth factors-encapsulating nanoliposomes. It is possible for the solubilized curcuminoids, growth factors, and/or encapsulating nanoliposomes to be made flexible or deformable in order to pass through the openings. Additionally or alternatively, their outer shell constituents can be made transferable, interchangeable or interdigitating with the surrounding stratum corneum so as to unload the actives on their way to permeating down the deeper skin area. In addition, excessive skin hydration, such as after a hot bath or shower, may induce temporary water channels in the stratum corneum to facilitate the passage of topically applied formulations. The preferred cross-sectionally shape of the microchannel will be circular or oval, as this allows for the use of extant needles.

When selecting the depth and diameter of appropriate microchannels, consideration should also be given to the comfort of the patient. Further, these microchannels will only be temporarily formed, so that application of the solubilized curcuminoids and/or nanoliposome-encapsulated growth factors or peptides should occur within the same time frame (i.e., less than 24 hours, less than two hours, or—most preferably—within 5 to 30 minutes after the fractional topical method (i.e., mechanical or energetic, as described herein) is performed).

Notably, the formulation does not enter the bloodstream, and the delivery methods are effectively intraepidermal so as to avoid permanent injury or significant bleeding. Also, despite relying upon needles in some embodiments, the creation of microchannels is distinct from intradermal injection, in which fluid is delivered via a syringe that immediately deposits the fluid into tissue (as opposed to subsequently applying the fluid).

At least the photosensitive curcuminoid(s) and, more preferably, the hair growth components and the photosensitive curcuminoid(s) are nano-encapsulated in bio-compatible material or materials to create delivery particles sized to cooperate with and pass through the microchannels mentioned above. The encapsulating material(s) should be bio-compatible material and capable of eventually releasing the encapsulated material. Lipids, liposomes, proteins, some polymers, and some combinations of all of these, and particularly nanoliposomes, are useful in this regard. Non-limiting example of such encapsulating materials can be found in U.S. Pat. Nos. 7,951,396 and 8,846,611, as well as United States Patent Publication 2016/0199498, which are all incorporated by reference herein. Preferably, the active components are individually encapsulated or complexed, and then mix them at the desired proportions noted above, although it may be possible to encapsulate the final formulation in its entirety.

The encapsulation reduces the formulation to an optimal, consistent size (i.e., "particle" formed by the encapsulation or complexed material). These particles are compatible with the selected delivery method. For example, with respect to mechanical methods such as micro-puncturing, the formulation (or some or all of the individual components of the formulation) is provided as, complexed with, or encapsulated in an appropriately biocompatible material. Such biocompatible forms include the free solutes of the photosensitive curcuminoids and/or the partial or complete capture of the photosensitive curcuminoids within polymeric micelles, polymeric/phospholipid composites, colloidal nanoparticles, and/or nanoliposomes.

The resulting particle has a particle size, preferably, that is less than the needle size (e.g., particles having diameters/sizes between 0.03 and 300 microns and, more preferably, between 0.2 and 200 microns can be delivered with 32-gauge needles as noted above), thereby allowing the formulation to permeate the top layer of skin and, ultimately, come into closer proximity to the hair root itself. Particle sizes can be measured based upon their diameter or greatest width according to microscopic visual inspection or commonly accepted techniques, such as laser diffraction, dynamic light scattering, or electrostatic attraction/repulsion between the particles.

Further, the nano-encapsulated particles present an exterior that is bio-compatible. This means that the particles can and will be absorbed into the microchannels (and/or pores of the skin) and penetrate to the desired depth in the epidermis. Negative pressure (e.g., vacuum or partial vacuum applied to the surface of the target area) and/or positive pressure (e.g., massage, increased air/fluid pressures at the surface of the target area) can also be employed to further encourage uptake.

Each component could be individually encapsulated and then mixed as part of the formulation or the entirety of the photosensitive enhancer and hair growth components can be encapsulated together. Still further, only selected components (e.g., the photosensitive curcuminoids) could be encapsulated, while others (e.g., inactive components) may be provided in solution, serum, powder, slurry/suspension, or some other form and then admixed with the encapsulated components.

With respect to the formulation itself, a plurality of synthetic peptides and growth factors associated with the three anagenic stages ("hair growth components") are provided. This mixture is specifically selected to facilitate the switch from catagen/telogenic phases back to the anagenic phase, as well as potentially helpful in promoting the induction of new follicular bulbs and, separately, actual growth around the induced bulbs. Also, the growth components may promote certain types of skin proteins and growth factors associated with the bulge cells during the anagen phase. Finally, the growth components can improve neo-vascularization and/or angiogenesis at or around the follicle during this stage. The disclosure of U.S. Pat. No. 10,894,074 is particularly helpful in this regard. Exemplary hair growth factors and peptides include follistatin (Wnt 7a), acidic fibroblast growth factor (aFGF), basic fibroblast growth factor (bFGF), protein rich plasma (PRP), human growth hormone (Hgh), vasoactive endothelial growth factor (VEFG), insulin-like growth factor (IGF), epidermal growth factor (EGF), keratin growth factor (KGF), vasoactive intestinal polypeptide (VIP), and/or thymosin beta 4, along with sh-polypeptide-7, sh-polypeptide-11, sh-polypeptide-1, sh-oligopeptide-1, sh-polypeptide-71, sh-oligopeptide-4, and/or sh-polypeptide-9. Combinations of two or more of these growth factors and peptides are possible, and all peptides are named according to the international nomenclature of cosmetic ingredients. Other solvents, surfactants, masking or smoothing agents, chelators, and hair conditioners could also be used. Also, to the extent treatment methods beyond hair growth are contemplated, it will be understood that "hair growth component" would be substituted by the active substance(s) germane to these other treatment methods, although the use of fractional topical delivery, nanoencapsulation, and excitation of the photosensitive curcuminoids are still retained.

In its most abstract form, the hair growth components address each of the stages identified by the inventor. Insofar as they are applied topically and locally (preferably by way of fractional topical delivery), it is possible to selectively apply the formulation to the areas desired to experience hair growth. In this manner, some of the shortcomings of oral medications or broad-based treatments can be diminished.

However, in contemplating ways to further improve the efficacy of this "all stages" approach to hair growth, the inventor further noted that, while photo dynamic therapies (PDT) are generally known in dermatology and other fields, no such approach is currently employed with respect to androgen receptors in the skin. PDT is a process by which a "photosensitizing" compound or drug is used to pretreat certain areas of the skin. The compound is then subsequently activated by specific wavelengths of light targeted at the treated area. In treatments for skin cancers, this activation of the photosensitive compound results in a cascading reaction of selective free radical oxidation in the treated area, thereby by killing off the cancerous cells without damage to the surrounding and otherwise healthy tissue.

Owing to their demonstrated ability to suppress androgen receptor signaling, curcumin served as a natural starting point of consideration for the present inventive formulations. Curcumin may be derived from the rhizome of turmeric, and it has known antioxidant, angiogenesis-inhibiting, and anti-inflammatory properties. Its pleiotropic effects suggest these properties flow from a plurality of targets and interacting macromolecular sites.

The inventor realized that curcumin and some of its structurally related analogues ("curcuminoids") exhibit the androgen-signaling inhibitory properties noted above and may be further activated by specific wavelengths of light. With reference to the disclosure below, curcumin, dimethyl curcumin (also referred to as ASCJ-9), demethoxycurcumin, and bis-demethoxycurcumin are active at red and/or infrared wavelengths that can be particularly effective for hair growth treatments. In fact, curcuminoids that respond to laser or fluorescent light at comparatively longer wavelengths of 600 to 900 nanometers are especially useful, and such wavelengths are already known to increase localized scalp circulation in their own right.

Any light source capable of selectively emitting the desired wavelength(s) should suffice. Thus, lasers, light-emitting diodes, and conventional light bulbs could be employed, along with appropriate optical filters to further narrow the specific, desired wavelengths.

One or a combination of photosensitive curcuminoids should be selected. A mixture of such curcuminoids can be specifically combined with light treatment at compatible and predetermined wavelengths. Also, by relying upon the red end of the spectrum, the stresses on the skin caused by exposure to ultraviolet light can be avoided.

Exemplary Structure for Preferred Photosensitive Curcuminoids

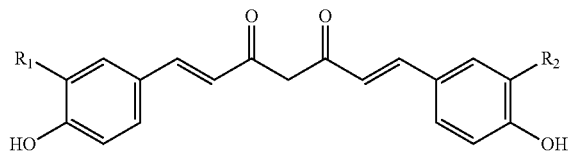

Curcumin $R_1$ = $OCH_3$, $R_2$ = $OCH_3$
Demethoxycurcumin $R_1$ = $OCH_3$, $R_2$ = H
Bisdemethoxycurcumin $R_1$ = H, $R_2$ = H The basic chemical structure of preferred, photoactive curcuminoids is shown above. The main curcuminoids are typically isolated from the Curcuma longa rhizome. Curcumin (CAS No. 458-37-7), dimethylcurcumin (CAS No.: 52328-98-0), demethoxycurcumin (CAS No.: 22608-11-3), and bisdemethoxycurcumin (CAS No.: 24939-16-0; 33171-05-0) are all particularly useful. To the extent applicable, tautomers of these structures may form and coexist when solubilized, and such tautomers are useful in certain aspects of the invention.

It must be noted that all curcuminoids do not universally exhibit the desired photoactive properties. For example, tetrahydrocurcumin (shown below, CAS no. 36062-04-1) only responds to white light and, therefore, is not a suitable candidate for use with this invention. Still other curcuminoids exhibit activity at shorter wavelengths in the blue part of the spectrum might be useful to kill bacteria and, in fact, have found use in acne treatments as a topical cream as noted above.

Even minor differences in conjugation, functional groups, and their relative positioning can have a significant impact on photosensitivity. Thus, care must be taken to avoid generalizations, and considerably experimentation and effort may be required to select appropriate curcuminoids.

Generally speaking, curcuminoids possessing a significant amount of conjugated bonds (i.e., the same or more than those found in curcumin) should prove useful, as may certain, stable salts of any of the photosensitive materials contemplated herein. In contrast, some other curcuminoids, such as tetrahydrocurcumin which has fewer conjugated bonds than the curcuminoids noted above, do not exhibit the desired photosensitivity (and/or photosensitivity at specific and useful wavelengths).

As noted above, the photosensitive curcuminoids are solubilized in a number of ways. They may be provided as free solutes (in conjunction with appropriate solvent(s)), mixed with polymeric micelles and/or polymeric/phospholipid composites, or formed as colloidal nanoparticles or nanoliposomes. In each instance, the curcuminoid assumes a bio-compatible form that is appropriate (in terms of size and chemical stability) that enables its use for the purposes described herein.

The active components (e.g., solubilized curcuminoids, growth factors, and/or peptides) can be incorporated in deformable vesicles, preferably comprising nanoliposomes containing biocompatible, "edge activators" such as surfactants and/or ethanol. These vesicles can be made with or without penetration enhancers (e.g., oleic acid, limonene, etc.).

When so constituted, the vesicles significantly aid permeation of the actives through the stratum corneum, such that the vesicles may overcome the size limitation imposed by the microchannels by a factor of up to 10. Collectively, these deformable vesicles and/or the encapsulated nanoliposomes are referred to herein as "biocompatible materials."

Notably, the fractional topical delivery used in combination with deformable nanoliposomes effectively eliminates long-term, unwanted staining or yellowing of the skin that is common to topical curcuminoid treatments in the prior art. However, during application of the curcuminoids above, a temporary and/or washable marker or colorant may be present to ensure positioning for accurate photoactivation.

One exemplary method includes the use of fractional topical delivery and subsequent irradiation relying upon red and/or infrared light is contemplated. The fractional delivery occurs by way of microchannels formed via laser or a plurality of miniaturized 32 gauge needles penetrating to a depth of approximately 50-300 microns, thereby avoiding pain receptors and major blood vessels. The inventive formulations administered before or/and after the fractional topical treatment comprise between 1 ng/ml (0.0000001 wt. %) and 1 mg/ml (0.1 wt. %), more preferably between 10 ng/ml (0.000001 wt. %) and 0.1 mg/ml (0.01 wt. %), and most preferably between 100 ng/ml (0.00001 wt. %) and 10

μg/ml (0.001 wt. %) of photosensitive curcuminoid(s), in combination with between 0.01 ppm (0.000001 wt. %) and 1,000 ppm (0.1 wt. %), more preferably between 0.5 ppm (0.00005 wt. %) and 200 ppm (0.02 wt. %), and most preferably between 1 ppm (0.0001 wt. %) and 100 ppm (0.01 wt. %) of hair growth components, and the balance comprising inert ingredients, fillers, and/or the nanoliposome materials themselves, although other formulations/iterations are also possible.

Once the inventive formulations are applied to the target area (usually as soon as is practical and preferably in less than an hour or less than 20 minutes), the target area is exposed to red or infrared light, preferably from a laser, so as to accumulate greater than 50 J/cm$^2$ of targeted area (i.e., treated skin). Thus, for an array of 272×5MW diode lasers, the treatment time should last for at least 5 minutes or more, and it should be initiated in less than 20 minutes, less than 12 minutes, or as soon as is practical after the inventive formulations and/or solution/serum (if the inventive formulations are admixed) is applied.

While hair growth is expected to have particular utility, the fractional topical delivery of photosensitive curcuminoids can be employed to promote bio-activity for various other reasons. For example, the fractional topical delivery methods can be resized to penetrate to the subdermal layer (but taking into account pain receptors) and/or to extend past the stratum corneam and epidermal skin barriers. In this manner, treatments can be developed to address the issues of cellulite, active and inflammatory acne, and other conditions.

Thus, the disclosure of U.S. Pat. No. 9,446,127 is incorporated. When combined with the fractional topical delivery, the inventive formulations comprising photosensitive curcuminoids and hair growth components, and light/radiation treatment methodologies of the current invention, the efficacy of acne treatments can be surprisingly and substantially improved. As with the inventive hair growth treatment, the administration of the acne-effective compounds is not by way of intradermal injection or topical application. Further, the use of short wavelength (e.g., blue or ultraviolet) light and/or of the longer wavelength red/infrared light according to the same principles as above, further distinguishes the invention.

In the same manner, rather than relying upon hair growth components, known treatments for cellulite, like collagenase and/or those disclosed in United States Patent Publication 2007/0224184 and/or 2015/0064165 (both incorporated by reference), can also be adopted. Again, these treatments (like those for acne) will hinge upon fractional topical delivery, the inventive formulations, and subsequent excitation via specific and targeted sources of light.

In view of the foregoing, various aspects of the invention can include any combination of the following features:
 selecting one or more photosensitive curcuminoids;
 combining the one or more photosensitive curcuminoids with a bio-compatible material to create a solubilized curcuminoid;
 applying the solubilized curcuminoid, in combination with one or more hair growth factors and/or peptides, to a targeted area of intraepidermal human skin;
 exposing the targeted area to a light source for a period of time that is effective to excite the photosensitive curcuminoids;
 wherein the applying the solubilized curcuminoid is by mechanical or energetic fractional topical delivery;
 wherein the light source has a wavelength between 600 and 900 nanometers; wherein at least two chemically distinct photosensitive curcuminoids are selected;
 wherein the photosensitive curcuminoids include at least one of: curcumin, dimethylcurcumin, demethoxycurcumin, and bis-demethoxycurcumin;
 wherein the hair growth factors and/or peptides are encapsulated in a nanoliposomal formulation with the photosensitive curcuminoid;
 wherein the solubilized curcuminoid has a diameter no larger than 300 microns;
 wherein the solubilized curcuminoids are applied by way of mechanical fractional topical delivery including the use of one or more intraepidermal needles;
 wherein the solubilized curcuminoids are applied by way of energetic fractional topical delivery and the light source emits only red and/or infrared wavelengths of light;
 wherein the exposing the treated area occurs within less than one hour after the applying the solubilized curcuminoid;
 wherein the applying the solubilized curcuminoid occurs within less than one hour after the mechanical or energetic fractional topical delivery;
 wherein the bio-compatible material is in a form of one selected from free solutes, polymeric micelles, polymeric/phospholipid composites, colloidal nanoparticles, and nanoliposomes;
 wherein the solubilized curcuminoid and the one or more hair growth factors and/or peptides are provided in a deformable vesicle;
 wherein the deformable vesicle includes at least one edge activator;
 wherein the deformable vesicle includes at least one penetration enhancer; and wherein the hair growth factors and/or peptides are encapsulated in a nanoliposomal formulation.

Although the present embodiments have been illustrated in the accompanying drawings and described in the foregoing detailed description, it is to be understood that the invention is not to be limited to just the embodiments disclosed, and numerous rearrangements, modifications and substitutions are also contemplated. Any such changes also fall within the scope of the appended claims or the equivalents thereof.

Unless otherwise indicated: (i) all measurements were conducted at ambient conditions, (ii) reported composition percentages are weight percentages, and (iii) molecular weights are be weight averages.

What is claimed is:

1. A method for promoting hair growth comprising:
 selecting one or more photosensitive curcuminoids;
 combining the one or more photosensitive curcuminoids in a bio-compatible form to create a solubilized curcuminoid;
 applying the solubilized curcuminoid, in combination with one or more hair growth factors and/or peptides, to a targeted area of intraepidermal layer of human skin without ingestion and without uptake into any blood vessels that are in and immediately adjacent to the targeted area; and
 exposing the targeted area to a light source for a period of time that is effective to excite the one or more photosensitive curcuminoids.

2. The method according to claim 1 wherein mechanical or energetic fractional topical treatment precedes the applying the solubilized curcuminoid to the targeted area.

3. The method according to claim 1 wherein the light source has a wavelength between 600 and 900 nanometers.

4. The method according to claim 1 wherein at least two chemically distinct photosensitive curcuminoids are selected.

5. The method according to claim 1 wherein the one or more photosensitive curcuminoids are at least one selected from the group consisting of: curcumin, dimethylcurcumin, demethoxycurcumin, and bis-demethoxycurcumin.

6. The method according to claim 1 wherein the hair growth factors and/or peptides are encapsulated in a nano-liposomal formulation with the one or more photosensitive curcuminoids.

7. The method according to claim 1 wherein the solubilized curcuminoid has a diameter no larger than 300 microns.

8. The method according to claim 1 wherein the solubilized curcuminoid are applied by way of mechanical fractional topical delivery including the use of one or more intraepidermal needles at an intraepidermal penetration of between 50 to 300 micrometers.

9. The method according to claim 1 wherein the solubilized curcuminoid are applied by way of energetic fractional topical delivery and the light source emits only red and/or infrared wavelengths of light.

10. The method according to claim 1 wherein the exposing the treated area occurs within less than one hour after the applying the solubilized curcuminoid.

11. The method according to claim 2 wherein the applying the solubilized curcuminoid to the targeted area occurs within less than one hour after the mechanical or energetic fractional topical treatment.

12. The method according to claim 1 wherein the biocompatible form is selected from the group consisting of: free solutes, polymeric micelles, polymeric/phospholipid composites, colloidal nanoparticles, and nanoliposomes.

13. The method according to claim 1 wherein the solubilized curcuminoid and the one or more hair growth factors and/or peptides are provided in a deformable vesicle.

14. The method according to claim 13 wherein the deformable vesicle includes at least one edge activator.

15. The method according to claim 13 wherein the deformable vesicle includes at least one penetration enhancer.

16. The method according to claim 1 wherein the hair growth factors and/or peptides are encapsulated in a nano-liposomal formulation.

17. A method for treating selected areas of skin to mitigate militate unwanted effects of localized androgens present therein, the method comprising:
  selecting one or more photosensitive curcuminoids;
  formulating the one or more photosensitive curcuminoids with one or more hair growth factors and/or peptides to create a photo-activated treatment compound;
  introducing the photo-activated treatment compound to a targeted intraepidermal layer of skin positioned between a surface layer of stratum corneum and a base layer of dermis by way of microchannels penetrating beyond stratum corneum, with the microchannels configured to avoid pain receptors in the dermis;
  wherein the introducing the photo-activated treatment does not include: i) ingestion of the photo-activated compound, and ii) uptake of the photo-activated treatment into any blood vessels that are in, above, below, or surrounding the targeted intraepidermal layer;
  wherein the formulating produces a photo-activated treatment compound having compatibility for passage through the microchannels; and
  exposing the surface layer immediately above the targeted intraepidermal layer to a light source for a period of time that is effective to excite the one or more photosensitive curcuminoids.

18. The method according to claim 17 wherein the introducing the photo-activated treatment compound includes mechanical creation of the microchannels by way of dilation, pressure, and/or temporarily puncturing the stratum corneum.

19. The method according to claim 17 wherein the introducing the photo-activated treatment compound includes energetic creation of the microchannels by way of electrical current, sonic energy, and/or electromagnetic radiation.

* * * * *